(12) United States Patent
Elfström et al.

(10) Patent No.: US 9,333,118 B2
(45) Date of Patent: May 10, 2016

(54) ABSORBENT ARTICLE COMPRISING A LIQUID DISCHARGE DETECTION SENSOR

(75) Inventors: Allan Elfström, Philadelphia, PA (US); Anders Gustafsson, Billdal (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 222 days.

(21) Appl. No.: 13/996,801

(22) PCT Filed: Dec. 20, 2011

(86) PCT No.: PCT/EP2011/073374
§ 371 (c)(1),
(2), (4) Date: Aug. 1, 2013

(87) PCT Pub. No.: WO2012/084924
PCT Pub. Date: Jun. 28, 2012

(65) Prior Publication Data
US 2013/0321007 A1    Dec. 5, 2013

(30) Foreign Application Priority Data
Dec. 23, 2010    (GB) .................................. 1022031.7

(51) Int. Cl.
*G08B 21/00*    (2006.01)
*A61F 13/42*    (2006.01)
*A61F 13/84*    (2006.01)

(52) U.S. Cl.
CPC ........... *A61F 13/42* (2013.01); *A61F 2013/424* (2013.01); *A61F 2013/428* (2013.01); *A61F 2013/8479* (2013.01); *A61F 2013/8482* (2013.01)

(58) Field of Classification Search
CPC ........ G01N 27/07; A61F 13/428; A61F 13/42
See application file for complete search history.

(56) References Cited

U.S. PATENT DOCUMENTS

| | | | |
|---|---|---|---|
| 6,774,800 B2* | 8/2004 | Friedman et al. | 340/573.5 |
| 7,221,279 B2* | 5/2007 | Nielsen | 340/604 |
| 2004/0207530 A1* | 10/2004 | Nielsen | 340/604 |
| 2005/0156744 A1 | 7/2005 | Pires | |

(Continued)

FOREIGN PATENT DOCUMENTS

| | | |
|---|---|---|
| AU | 63393/94 A | 12/1994 |
| CN | 101446565 A | 6/2009 |

(Continued)

*Primary Examiner* — Van Trieu
(74) *Attorney, Agent, or Firm* — Drinker Biddle & Reath LLP

(57) ABSTRACT

An absorbent article for absorbing liquid discharge of a wearer when worn in the crotch region includes an absorbent core for doing the absorbing of the liquid discharge. A conductive layer is in electrical contact with the absorbent core. The article includes at least one set of first and second electrical contacts secured in intimate physical and electrical contact with the conductive layer such that when an electric potential is applied between the first and second electrical contacts, an electric current travels between them and through the conductive layer in such a way so as to follow a first relatively high impedance path along the conductive layer when the absorbent core is dry and a relatively low impedance path when the absorbent core is wet. This system allows a system verification check, even in the dry state, and the determination of the extent of the wet portion of the absorbent core.

20 Claims, 1 Drawing Sheet

(56) References Cited

U.S. PATENT DOCUMENTS

| | | |
|---|---|---|
| 2007/0035405 A1 | 2/2007 | Wada et al. |
| 2007/0083174 A1* | 4/2007 | Ales et al. .................... 604/361 |
| 2007/0252713 A1* | 11/2007 | Rondoni et al. ........... 340/573.5 |
| 2007/0270774 A1 | 11/2007 | Bergman et al. |
| 2008/0051745 A1 | 2/2008 | Long et al. |
| 2008/0132859 A1 | 6/2008 | Pires |
| 2009/0315728 A1* | 12/2009 | Ales et al. .................... 340/604 |

FOREIGN PATENT DOCUMENTS

| | | |
|---|---|---|
| JP | 2000-139983 A | 5/2000 |
| JP | 2000-342615 A | 12/2000 |
| JP | 2010-172426 A | 8/2010 |
| WO | WO-2007/087674 A1 | 8/2007 |

* cited by examiner

US 9,333,118 B2

ABSORBENT ARTICLE COMPRISING A LIQUID DISCHARGE DETECTION SENSOR

CROSS-REFERENCE TO PRIOR APPLICATION

This application is a §371 National Stage Application of PCT International Application No. PCT/EP2011/073374 filed Dec. 20, 2011, which claims priority to GB 1022031.7, filed Dec. 23, 2010, both of which are incorporated herein in their entirety.

TECHNICAL FIELD

The field of disclosure concerns an absorbent article including a liquid discharge detection sensor.

BACKGROUND

It is known in the art to provide an absorbent article with a liquid discharge detection sensor in order to detect when the absorbent article has been wetted by a wearer urinating. One example of such a prior art disclosure is AU-B-63393/94. According to this document, a urine detector includes two terminals between which a moisture receptive strip or pad is located. When the moisture receptive strip or pad is dry, the electrical conductivity between the terminals is substantially zero. The conductivity increases sharply when moistened by urine. The detector thus acts as a switch for indicating when an absorbent article needs changing.

Further information on the urination event may be desirable for an absorbent article manufacturer or for a care giver concerning the nature of the urination.

SUMMARY

There is provided an absorbent article for absorbing liquid discharge of a wearer when worn in the crotch region, the absorbent article including an absorbent core for doing the absorbing of the liquid discharge, a conductive layer in electrical contact with the absorbent core and first and second electrical contacts with the conductive layer such that when an electric potential is applied between the first and second electrical contacts, an electric current travels between them through the conductive layer in such a way so as to follow a first relatively high impedance path along the conductive layer when the absorbent core is in a dry state and to follow a relatively low impedance path, when the absorbent core is in a wetted state from the liquid discharge, that at least partially diverts through the absorbent core, wherein the change in impedance from the dry core state to the wetted core state is measurable.

The two alternative current flow paths implicitly require the impedance of the conductive layer to be appropriately chosen to enable the effect to occur. Thus, if the conductive layer is of too low an impedance, then the current will only flow along the conductive layer whether the absorbent core is wet or dry. Further, the impedance of the conductive layer has to be of lower impedance than the dry absorbent core to have the undiverted current flow path when the absorbent core is dry.

The absorbent article allows a system verification check to be done since, even in the dry state, a conductive return path is established between the first and second contacts and along the conductive layer. Further, the change in impedance when diverted depends on the extent of the absorbent core in electrical contact with the conductive layer between the contacts that are wet. Thus, the system enables not only a wet or dry state between the contacts to be determined but also the proportion of the current flow path that travels through a wet core, which is indicative of the extent of the wet portion of the absorbent core. This is useful information in determining absorbency performance of the absorbent article.

In particular embodiments, there is a plurality of sets of first and second contacts distributed longitudinally and/or laterally about the conductive layer so as to allow better localisation of a portion of the absorbent core that is in the wetted state.

In particular embodiments, the sets of contacts and the conductive layer are distributed longitudinally along the absorbent core at least about 25%, 30%, 40%, 50%, 60%, 70% or even 80% of the full longitudinal extent of the absorbent core.

In particular embodiments, the contacts and the conductive layer are arranged so as to pass electrical current laterally and/or longitudinally through the absorbent core when it is in a wetted state along at least 25%, 30%, 40%, 50%, 60%, 70%, 80% or even 90% of the full lateral and/or longitudinal extent of the absorbent core. This feature will provide good coverage of the absorbent core with the liquid discharge detector for determining the extent and the locality of the liquid discharge.

In particular embodiments, the contacts are in the form of linear contacts substantially aligned with a lateral axis of the absorbent core, wherein the linear contacts are longitudinally spaced from one another. This provides liquid discharge detection wherever the insult occurs along the lateral extent of the contacts and longitudinal determination of the liquid discharge's locality and extent.

In particular embodiments, a lateral extent of each of the contacts is at least about 30%, 40%, 50%, 60%, 70%, 89% or even 90% of the full lateral extent of the absorbent core at the location in the absorbent core of the respective contact.

In a certain embodiment, the conductive layer covers fully the contacts when the absorbent article is viewed in plane and laid out flat.

In particular embodiments, the conductive layer is positioned between an underside of the absorbent core and a liquid impermeable backsheet of the absorbent article. In yet more particular embodiments, the contacts are positioned on the underside of the conductive layer.

In a certain embodiment, the absorbent core is captured between a back sheet and a top sheet, wherein the top sheet is configured to allow the liquid discharge to enter the absorbent core and the back sheet is configured to prevent escape of the liquid discharge from the absorbent core, wherein the conductive layer is provided by the back sheet, or a portion of it, and the contacts are applied to the back sheet. The back sheet is in contact with the absorbent core and thus is able to be in conductive relation with it. In particular embodiments, the back sheet is made of, or at least partly of, a conductive polymer, thereby enabling it to have some stretchability. The contact could be applied to the back sheet by an adhesive layer secured to the back sheet. Alternatively, the top sheet, absorbent core and back sheet laminate could be removably applied to a reusable absorbent article chassis of the absorbent article that is mountable to a wearer, and which may include fastening means for securing the chassis about a waist of the wearer, wherein the chassis includes the contacts, which are brought into electrical engagement with the conductive back sheet when the top sheet, absorbent core and back sheet is removably applied to the chassis of the absorbent article. This enables the liquid discharge detection system to be implemented less expensively since the contacts and associated circuitry are part of a reusable chassis. The back sheet can be breathable but still considered liquid impermeable, if the liquid form of the liquid discharge is prevented from escaping from the laminate therethrough.

In a second aspect, there is provided a system including an absorbent article as defined above and a measurement unit that is configured to apply a potential between the first and second contacts and to measure an electrical property that changes in dependence on whether the relatively high impedance flow path is taken or the relatively low impedance flow path is taken.

In a certain embodiment, the extent of the electrical property is measured and recorded by the measurement unit being so configured.

In particular embodiments, the electrical property measurements are recorded over time by the measurement unit. This allows the spread of the liquid discharge event to be monitored.

In a certain embodiment, in the case where the absorbent article includes a plurality of sets of the first and second contacts, the measurement unit is configured to apply a potential between the first and second contacts of each of the sets and to measure the electrical property for each of the sets.

In particular embodiments, an analysis unit is configured to process the measured electrical property data and determine an extent along the absorbent core that the liquid discharge has spread.

In particular embodiments, the analysis unit is configured to determine the locality of a wet portion of the absorbent core based on which of the sets of first and second contacts have been activated.

Further, the analysis unit can be configured to determine a volume of the liquid discharge based on the extent of the wet portion of the absorbent core.

DETAILED DESCRIPTION OF PREFERRED EMBODIMENTS

Figure 1:
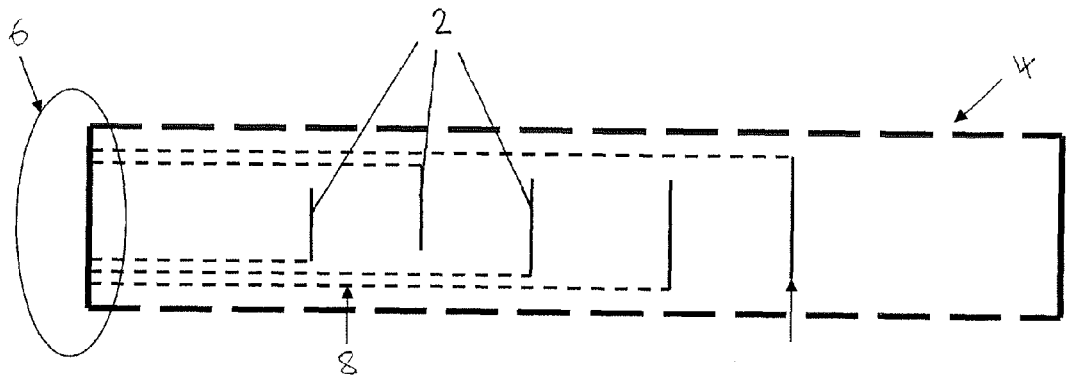
FIG. 1 discloses an arrangement of liquid discharge sensors and a conductive layer that are to be associated with an absorbent core of an absorbent article.

FIG. 1 discloses a plane view of an arrangement of conductive contacts 2 secured in electrical and physical contact with a conductive layer 4. The arrangement of the contacts 2 and the conductive layer 4 is to be placed in contact with an underside of an absorbent core with the length of the conductive layer 4 aligned with the length of the absorbent core. Ideally, the conductive layer 4 is to be at least as large in length and width as the absorbent core so as to be in intimate contact with the absorbent core over a complete area of the absorbent core. However, the conductive layer 4 can, in some circumstances, be somewhat smaller than the absorbent core when only certain areas of the absorbent core are relevant for measurement purposes.

The conductive layer 4 is in the form of a rectangular sheet and the contacts 2 are in the form of linear contacts extending across at least half of the width of the conductive layer 4. In the shown embodiment, there are five contacts 2 that are longitudinally spaced from one another along the conductive layer 4 and which are longitudinally distributed over at least half of the conductive layer 4. The number of contacts can vary and is to be chosen according to the desired accuracy of the measurement etc.

Each of the contacts 2 is connected to a measurement unit 6 by a respective lead that is insulated from the conductive layer 4 and the absorbent core. The measurement unit 6 is for applying a voltage between adjacent pairs of the contacts 2 so as to pass a current from a first of the pair of contacts to a second of the pair of contacts along the conductive layer 4. The current may be diverted through the absorbent core when the absorbent core is wet, as will be described more fully in the following. The measurement unit 6 applies a voltage between each adjacent pair of contacts 2 and takes and records an impedance reading for the current flow path for each of the adjacent pairs of contacts 2. If desired for measurement purposes, a voltage can also be applied between two contacts that are not directly adjacent each other.

Figure 2:
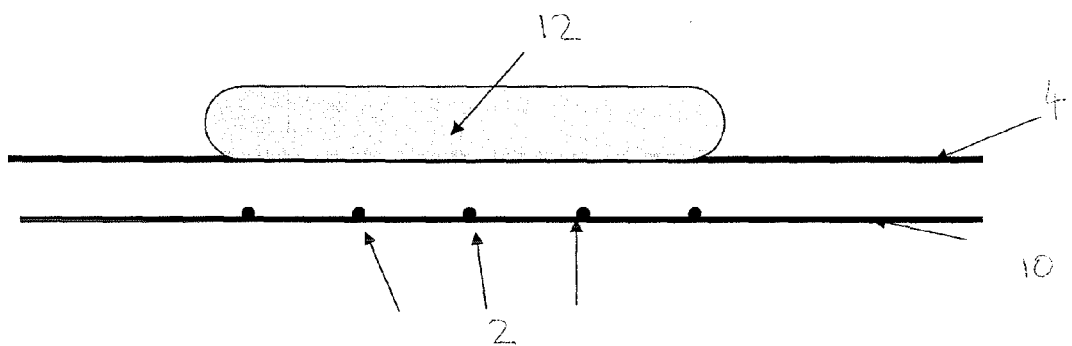
FIG. 2 shows a longitudinal cross-section of a laminate of an absorbent core, a conductive layer positioned underneath the absorbent core and a plurality of contacts on a backsheet of an absorbent article.

In FIG. 2, the arrangement of contacts 2 and a conductive layer 4 is shown in combination with an absorbent core 12 and a liquid impermeable backsheet 10 of the absorbent article. In FIG. 2, the contacts 2 and the conductive layer 4 are shown spaced apart from one another in a direction normal to the conductive layer 4 for clarity reasons. In reality, the contacts 2 will be in intimate physical and electrical contact with the conductive layer 4. A longitudinal cross-section of the laminate of an absorbent core 12, a conductive back layer 4 and the backsheet 10 is shown in FIG. 2. As can be seen, the conductive layer 4 is applied to an underside of the absorbent core 12, the contacts 2 are applied to a top side of the backsheet 10. The contacts 2 may be in form of conductive threads, for example, metallic wires or non-conductive threads that are coated with a conductive material or, in a certain embodiment, conductive print on the liquid impermeable backsheet 10. The conductive layer 4 may be made of a polymeric material that is conductive but with a high resistance to conduction as compared to the wet absorbent core and with low resistance to conduction as compared to the dry absorbent core.

In FIGS. 1 and 2, a top sheet of the absorbent article is not shown, nor are other conventional details of the absorbent article. In practice, the conceptual system shown in FIGS. 1 and 2 is integrated with a conventional absorbent article such as an adult incontinence garment in the preferred form or perhaps even a baby or toddler diaper or a sanitary towel.

Figure 3:
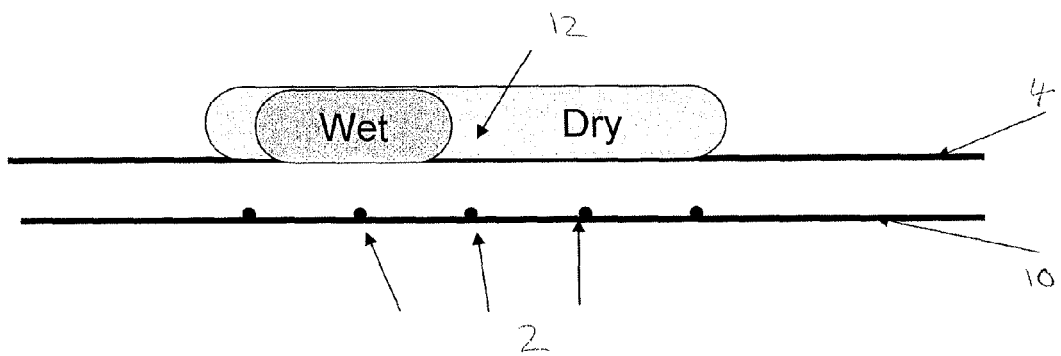
FIG. 3 shows the same arrangement as that of FIG. 2 but wherein a longitudinal portion of the absorbent core has been wetted by a liquid discharge.

Referring to FIGS. 2 and 3, an example use of the liquid discharge detection system can be understood. In FIG. 2, the absorbent core 12 is dry. Accordingly, when the measurement unit 6 applies an electrical potential between each of the adjacent pairs of contacts 2, electric current flows from a first contact of the adjacent pair to a second contact of the adjacent pair 2 along the conductive layer 4. The measurement unit 6 thus measures an impedance largely determined by the conductive layer 4, which is made of a relatively high resistance conductive material. The measurement unit 6 or an analysis unit (not shown) can compare the impedance measured for that pair of contacts 2 to the impedance expected when the absorbent core 12 is dry and determine that the absorbent core is dry between that pair of adjacent contacts 2. The measurement unit 6 is configured to cycle through each of the adjacent pairs to carry out the measurement and perhaps also perform the comparison to determine a dry state for each of the adjacent pair of contacts 2. A different cycle may be used if a voltage is applied to pairs of contacts that are not directly adjacent each other.

The measurement unit 6 or an analysis unit is also able to determine that the system is functioning properly since a return current is received, thereby indicating that there are no breaks in the conductive paths between an adjacent pair of contacts 2 and also that the impedance corresponds to an expected level, thereby indicating that the system is functioning properly, i.e. that the absorbent core 12 has not come away from the conductive layer 4 and is instead in consistent intimate contact therewith.

Further, the measurement unit 6 is configured to perform the cycle of measurements at regular or irregular intervals and record the impedance measurement taken so that an analysis unit can subsequently determine an absorbency performance of the absorbent core 12, which is particularly interesting as it allows the spread of liquid discharge to be observed over time as well as separate liquid discharge events to be observed.

In the illustration of FIG. 3, the absorbent core 12 is wet over a partial longitudinal extent of the absorbent core 12 and is dry over the remainder of absorbent core 12. The measurement unit 6 is configured to apply an electric potential between first and second contacts 2 of each adjacent set of contacts 2. Referring to the contacts 2 as first, second, third, fourth and fifth when reading from the left hand side in the embodiment of FIG. 3, the measurement unit 6 will pass a current between the first and second contacts 2 that will pass along the conductive layer 4 adjacent where the absorbent core 12 is dry and the current will then pass through (in a direction normal to the plane of the conductive layer 4) the layer 4 into the wet portion of the absorbent core in order to follow a path of least resistance since the wet absorbent core has greater conductivity than the conductive layer 4. The electric current will then pass back through the conductive layer 4 in returning to the second contact 2. The overall impedance of this partially diverted conductive path as measured by the measurement unit 6 will be less than the impedance measured when the absorbent core 12 is dry between the first and second contacts, thereby indicating that the absorbent core 12 is wet. The impedance measured by the measurement unit 6 will also be greater than if the absorbent core 12 was wet along the full length of the path between the first and second contacts 2 since the electric current must at least partially travel along the resistive conductive layer 4. Accordingly, the measurement unit 6 or an analysis unit reading the data recorded by the measurement unit 6 is able to determine that the area between the first and second contacts 2 of the absorbent core 12 is partially, but not fully wet. A similar deduction can be made as a result of the measurement unit 6 applying a potential between the second and third contacts 2. When the measurement unit 6 applies a potential between the third and fourth contacts 2 and the fourth and fifth contacts 2, the impedance result is indicative of the absorbent core 12 being in a dry state at these locations.

Accordingly, an analysis of the data recorded by the measurement unit 6, perhaps performed by a software implemented analysis unit, will be able to determine that the absorbent core 12 is partially wet between the first and second contacts 2 and the second and third contacts 2. Further, the particular impedance measured is indicative of how far along the conductive layer 4 the wet portion has spread in the absorbent core 12, thereby allowing an analysis to be able to determine to an accurate termination not only of the locality of the wet portion of the absorbent core 12 between the first and third contacts 2, but also the extent (in terms of length or area) of the wet portion in this region, thereby allowing the system to accurately determine the location of the wet portion and its extent. The location and extent data can be used by an analysis unit to calculate an estimated volume of the wet portion of the absorbent core 12. The volume data, area data, and location data for the wet portion of the absorbent core 12 is interesting both for a care giver and for a manufacturer of absorbent articles in assessing the absorbency performance of the absorbent core 12. Further, because the measurement unit 6 takes and records measurements at regular intervals, for example, every second or even less, the spread of the wet portion in the absorbent core 12 over time is able to be analysed, which is also highly useful data in analysing the absorbency performance of an absorbent core 12.

The invention claimed is:

1. An absorbent article for absorbing liquid discharge of a wearer when worn in the crotch region, the absorbent article comprising:
   an absorbent core for absorbing the liquid discharge,
   an electrically conductive layer in electrical contact with the absorbent core, and
   at least one set of first and second electrical contacts in contact with the electrically conductive layer such that when an electric potential is applied between the first and second electrical contacts, an electric current travels between them and through the electrically conductive layer in such a way so as to follow a first relatively high impedance path along the electrically conductive layer when the absorbent core is in a dry state and to follow a relatively low impedance path when the absorbent core is in a wetted state from the liquid discharge that at least partially diverts through the absorbent core,
   wherein the change in impedance from the dry core state to the wetted core state is measurable,
   wherein each of the first electrical contact and the second electrical contact extend longitudinally and/or laterally over at least 25% of the absorbent core, and
   wherein there are a plurality of sets of first and second contacts distributed longitudinally and/or laterally about the electrically conductive layer.

2. The absorbent article according to claim 1, wherein the sets of contacts and the electrically conductive layer are distributed longitudinally along the absorbent core at least about 25% of the full longitudinal extent of the absorbent core.

3. The absorbent article according to claim 1, wherein the contacts and the electrically conductive layer are arranged so as to pass electrical current laterally and/or longitudinally through the absorbent core when it is in a wetted state along at least 25% of the full lateral and/or longitudinal extent of the absorbent core.

4. The absorbent article according to claim 1, wherein the contacts are in the form of linear contacts aligned with a lateral axis of the absorbent core, wherein the linear contacts are longitudinally spaced from one another.

5. The absorbent article according to claim 1, wherein the electrically conductive layer covers fully the contacts when the absorbent article is viewed in plane and laid out flat.

6. The absorbent article according to claim 1, wherein the electrically conductive layer is positioned between an underside of the absorbent core and a liquid impermeable backsheet of the absorbent article.

7. The absorbent article according to claim 1, wherein the contacts are positioned on the underside of the electrically conductive layer.

8. The absorbent article according to claim 1, wherein the absorbent core is captured between a back sheet and a top sheet, wherein the top sheet is configured to allow the liquid discharge to enter the absorbent core and the back sheet is configured to prevent escape of the liquid discharge from the absorbent core, wherein the electrically conductive layer is provided by the back sheet, or a portion of it, and the contacts are applied to the back sheet.

9. The absorbent article of claim 8, wherein the back sheet is made of, or at least partly of, a conductive polymer.

10. The absorbent article of claim 9, wherein the top sheet, absorbent core and back sheet laminate is removably applied to a re-usable absorbent article chassis of the absorbent article that is mountable to a wearer, and which may include a fastening for securing the chassis about a waist of the wearer, wherein the chassis includes the contacts, which are brought into electrical engagement with the electrically conductive back sheet when the top sheet, absorbent core and back sheet is removably applied to the chassis of the absorbent article.

11. A system comprising the absorbent article according to claim 1, and a measurement unit that is configured to apply a potential between the at least one set of first and second contacts and to measure an electrical property that changes in dependence on whether the relatively high impedance flow path is taken or the relatively low impedance flow path is taken.

12. The system of claim 11, wherein the extent of the electrical property is measured and recorded by the measurement unit being accordingly configured to do so.

13. The system of claim 11, wherein the measurement unit is configured to record the electrical property measurements over time.

14. The system of claim 11, wherein there are a plurality of sets of first and second contacts distributed longitudinally and/or laterally about the electrically conductive layer in the absorbent article, and-wherein the measurement unit is configured to apply a potential between the first and second contacts of each of the sets and to measure the electrical property for each of the sets.

15. The system of claim 14, wherein an analysis unit is configured to determine the locality of a wet portion of the absorbent core based on which of the sets of first and second contacts have been activated.

16. The system of claim 11, wherein an analysis unit is configured to process the measured electrical property data and determine an extent along the absorbent core that the liquid discharge has spread.

17. The system of claim 16, wherein the analysis unit is configured to determine a volume of the liquid discharge based on the extent of the wet portion of the absorbent core.

18. The absorbent article of claim 1, wherein a measurement of impedance is obtained from a voltage applied between the first contact in a first of the plurality of sets and the second contact in a second of the plurality of sets, wherein the first contact in the first plurality of sets and the second contact in the second plurality of sets are separated by at least one other contact from the plurality of sets.

19. The absorbent article of claim 1, wherein the first electrical contact is connected to a first lead that is insulated from the electrically conductive layer and the second electrical contact is connected to a second lead that is insulated from the electrically conductive layer, and wherein the first and second electrical contacts are substantially parallel and substantially orthogonal to the first and second insulated leads.

20. An absorbent article for absorbing liquid discharge of a wearer when worn in the crotch region, the absorbent article comprising:
   an absorbent core for absorbing the liquid discharge,
   an electrically conductive layer in electrical contact with the absorbent core, and
   at least one set of first and second electrical contacts with the electrically conductive layer such that when an electric potential is applied between the first and second electrical contacts, an electric current travels between them and through the electrically conductive layer in such a way so as to follow a first relatively high impedance path along the electrically conductive layer when the absorbent core is in a dry state and to follow a relatively low impedance path when the absorbent core is in a wetted state from the liquid discharge that at least partially diverts through the absorbent core,
   wherein the change in impedance from the dry core state to the wetted core state is measurable,
   wherein the contacts are in the form of linear contacts aligned with a lateral axis of the absorbent core, wherein the linear contacts are longitudinally spaced from one another.

* * * * *